United States Patent [19]

Cohen

[11] 4,274,173

[45] Jun. 23, 1981

[54] POWER DRIVEN BRUSH ASSEMBLY

[76] Inventor: Howard Cohen, 2791 W. 5th St., Brooklyn, N.Y. 11224

[21] Appl. No.: 54,943

[22] Filed: Jul. 5, 1979

[51] Int. Cl.³ .............................................. A46B 13/02
[52] U.S. Cl. ..................................... 15/28; 15/167 R; 15/179
[58] Field of Search ................... 15/28, 29, 167 R, 179

[56] References Cited

U.S. PATENT DOCUMENTS

| 361,806 | 4/1887 | Ballard | 15/167 R |
|---|---|---|---|
| 3,242,516 | 3/1966 | Cantor | 15/28 |
| 3,848,336 | 11/1974 | Copeland | 15/28 X |

FOREIGN PATENT DOCUMENTS 490892 8/1938 United Kingdom ................ 15/167 R

Primary Examiner—Christopher K. Moore
Attorney, Agent, or Firm—Robert W. Fiddler

[57] ABSTRACT

A power driven brush assembly for cleaning teeth or the like. The brush assembly is formed with a hollow handle element containing drive means coupled to a power transmission extending from the handle element through a handle extension which carries a plurality of brush supporting members remote from the handle element. A plurality of brushes, one for each brush supporting member, is provided, with at least one of said brushes contoured with a cup-shaped cavity at a free end thereof remote from said brush support to implement the facility with which the outer edges of the brush may be bent to approximate the contours of the surface to be brushed. A method based on the same inventive concept is also disclosed for implementing the facility with which a surface may be brushed. This is accomplished by forming a plurality of brushing members with relatively unrestrained brushing portions free to flex to and from a longitudinal axis of the brushing member, and mounting the brushing members for rotation about the longitudinal axis thereof; and thereafter driving the brushing members to bring the relatively unrestrained brushing portions over the surface to be brushed with adjacent brushing members rotating in opposite directions.

3 Claims, 5 Drawing Figures

POWER DRIVEN BRUSH ASSEMBLY

BACKGROUND OF THE INVENTION

This invention relates to the art of power driven brushes of the type generally employed as toothbrushes or the like.

A variety of such power driven brushes have been evolved with a view to implementing the facility with which teeth or the like may be brushed. Where such brushes are employed for dental hygiene, it is found that with the same expenditure of time, the average individual can attain greater thoroughness of brushing, and hopefully improved dental hygiene, as compared to that available with a manual brush. Further, by minimizing required physical exertion and time, and/or providing a relatively self-acting piece of equipment, it is hoped that the user will find the chore more palatable.

Though power driven toothbrushes employing either self-contained electric motors, or water driven turbines, have previously been employed, and though such previously evolved brushes appear to have greatly enhanced the facility with which an individual can care for his or her own teeth, these previously evolved brushes still do not serve to clean all of the complexly contoured surfaces of the conventional tooth, both because of the limited range of motion of the brush, and because of the contours of the brush, which do not always approximate the surfaces of the tooth to be cleaned.

Thus, prior art power driven toothbrushes have generally employed a motor containing handle coupled to a brush to either reciprocate it along a longitudinal linear path or transverse linear path. The user further compounds the locus of movement of the brush by manually manipulating the brush to augment the paths of movement provided by the motor drive, and though this complexity of movement does indeed significantly improve cleaning as compared to that with a conventional manual toothbrush, it is found that plaque and the like debris often remains on the tooth surface, primarily because of the lack of contact of the brush surfaces with the tooth surfaces.

Professional brushing equipment employed by dentists, dental hygienists, and the like, utilize rotary brushes of relatively small diameter, with the rotating brush subject to positioning in the various crevices of the teeth. Such rotary toothbrushes are not available to the average individual, and even if available, would not be usable, since the careful manipulation of the relatively small brush over the various surfaces of the tooth is not something which the average individual is capable of performing.

BRIEF DESCRIPTION OF THE INVENTION

It is with the above considerations in mind that the present improved brush assembly has been evolved, a brush particularly suitable for use in forming a power driven toothbrush serving to increase the facility with which the relatively irregular contours of teeth may be easily brushed by the average individual cleaning his own teeth.

It is accordingly among the primary objects of this invention to provide an improved power driven brush assembly facilitating the ability of an individual to satisfactorily clean the complexly contoured surfaces of his or her own teeth.

Another object of the invention is to provide an improved power driven brush assembly, in which the brush elements lend themselves to approximating with a greater degree of facility than previously available the contours of the surface to be brushed.

An additional object of the invention is to provide a power driven brush assembly for use in cleaning relatively complex and irregular surfaces.

It is also an object of the invention to provide an improved method for implementing the facility with which a surface may be brushed.

These and other objects of the invention which will become hereinafter apparent, are achieved by forming a hollow handle with drive means in the handle. A hollow extension from the handle element contains a power transmission for transferring power from the drive means to a plurality of rotatably mounted brush supporting elements arranged on the free end of the extension. A brush is supported on each supporting element, and the brushes are formed with a cup-shaped cavity at the free end thereof to implement bristle flexing to and from the axis of rotation. The method embodying the inventive concept serves to implement the facility with which a surface may be brushed and comprises the steps of forming a brushing member with relatively unrestrained brushing portions free to flex to and from the longitudinal axis of the brushing member, and mounting the brushing member for rotation, with adjacent segments of adjacent brushes moving in opposite directions.

A feature of the invention resides in the formation of the cup-shaped cavity at the end of a rotatably mounted brush, thus providing upstanding brushing surfaces spaced from the axis of rotation which are free to flex to and from the axis of rotation, as compared to a conventional brush where the central brushing elements are restrained by those surrounding it, so that the amount of flexing is limited.

Another feature of the invention resides in the utilization of a plurality of brushes, the adjacent segments of which move in a direction opposite to that of an adjacent brush, thus facilitating the ability to dislodge material from the surface to be cleaned.

BRIEF DESCRIPTION OF THE DRAWINGS

The particular details of the best mode contemplated by the inventor for carrying out the invention, and of the manner and process of making and using same so as to enable those skilled in the art to make and use same, will be described in full, clear, concise and exact terms, in conjunction with the accompanying drawings, wherein.

DESCRIPTION OF PREFERRED EMBODIMENT OF THE INVENTION

Figure 1:
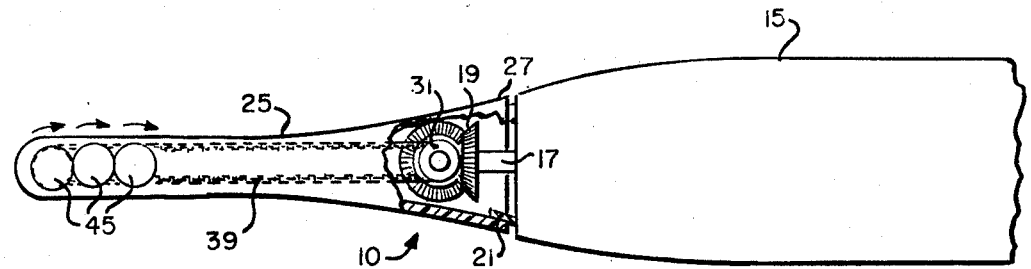
FIG. 1 is a view of a power driven brush made in accordance with the teachings of the invention, looking down at the brush ends, and with portions of the extension broken away to reveal the power transmission for transmitting power from the motor to the brush supporting shafts.
Figure 2:
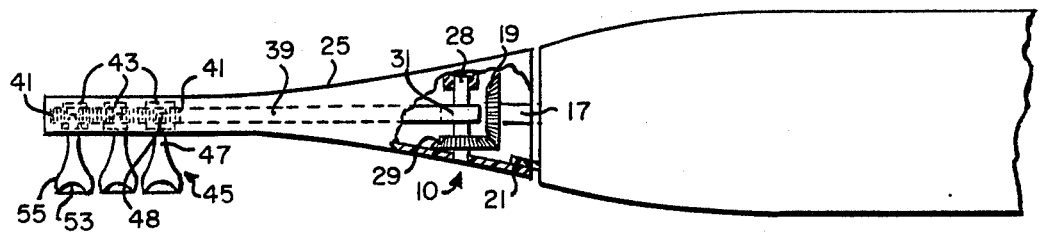
FIG. 2 is a side view taken of FIG. 1 showing the brushes in elevation with parts of the extension broken away to show the brush interconnection with the driven brush supporting wheel members.

Referring now more particularly to the drawings, where like numerals in the various FIGS. will be employed to designate like parts, in the embodiment of the invention illustrated in FIGS. 1 and 2, the brush assembly 10 illustratively shown as formed of a size suitable for cleaning teeth is provided with a hollow handle element 15, containing a conventional electrical motor (not shown) coupled to a drive shaft 17. The drive shaft 17 is provided with a driving bevel gear 19 at the end thereof rotating in a plane perpendicular to the axis of the drive shaft 17. An annular collar 21 is formed on the free end of handle element 15, extending outwardly therefrom.

Hollow handle extension 25 formed of plastic material or the like, is contoured, as illustrated in the drawing, with a flared end 27 dimensioned to transition to the collar bearing end of handle 15. The interior of flared end 19 is dimensioned to frictionally engage annular collar 21, so as to provide for a selectively detachable friction coupling between the extension 25 and the handle 15.

Supported within hollow handle extension 25 on journal 28, which is mounted for rotation in the extension 25, is bevel gear 29. Journal 28, as best seen in FIG. 2 is mounted in housing 25, preferably by embedding the free ends of the journal in the material of the housing extension. Bevel gear 29 meshes with and is driven by driving gear 19.

A driving spur gear 31 is mounted on shaft 27 for rotation therewith, and a drive belt 39 preferably having rack teeth thereon is trained over spur gear 31 for movement thereby.

At the free end of handle extension 25, three driven brush supporting wheel members 41, preferably formed with gear teeth on the circumferential edge thereof, are mounted for rotation in the housing extension. These driven brush supporting wheel members 41 are formed with journals 43 and 44 arranged for rotation in bearing sockets formed in the housing extension 25 on opposed sides of the wheel members. The wheel members themselves are formed with recesses 48 to frictionally receive the brush members 45, hereafter described.

Figure 3:
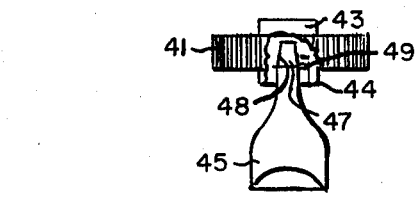
FIG. 3 is an enlarged detail view with parts broken away of a brush supporting wheel, showing a brush in position.

Each brush member 45, as best seen in FIG. 3, is formed with a tapered plug end 47 adapted for insertion into the recess 48 in brush supporting wheel member 43 for frictional engagement thereby. A drive pin 49 may be formed along plug end 47 riding in a slot in recess 48 if desired.

The brush members are contoured as illustrated with a cup-shaped cavity 53 and axially extending circumferentially arranged brush surfaces 55 spaced from the axis of rotation.

Figure 4:
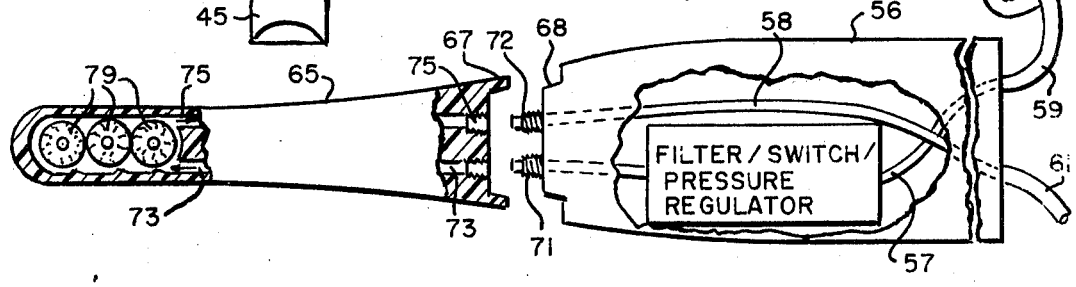
FIG. 4 is a schematic view with parts broken away showing an alternate embodiment in which the brush supporting wheels are formed as water driven turbines permitting use of water as a power source.
Figure 5:
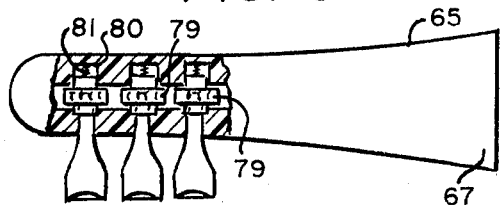
FIG. 5 is a view of the handle extension of the FIG. 4 embodiment with parts broken away, showing the brushes and brush supporting wheels in elevational view.

In the embodiment of the invention illustrated in FIGS. 4 and 5, handle 56, shown with parts broken away to the right in FIG. 4, is provided with a water supply line 57, and a water return line 58. Water supply line 57 is connected to a water supply hose 59 leading to a faucet connection (not shown) of conventional type, serving to provide a water tight coupling between hose 59 and a sink faucet outlet such as conventionally available in the usual bathroom, where the toothbrush is to be employed. Water return line 58 is coupled to a flexible discharge hose 61 of a length such as to permit it to hang with its discharge end in a sink.

A hollow handle extension 65 is formed of a contour much like handle extension 25 provided with a transitioning flared end 67 dimensioned to provide a friction coupling to flange 68 on handle 56.

Hose coupling 71 extends from the water supply line 57, and hose coupling 72 extends to the water return line 58.

The hollow handle extension 65 is formed with a water supply channel 73 formed with an inlet end adapted for engagement with hose coupling 61, with channel 73 leading past brush supporting turbine wheels 79, which are formed with journals engaging in recesses 80 providing bearings for the turbine journals, much like the mounting of the brush supporting gear wheel members 41 in the FIG. 1 and 2 embodiments. A return water flow channel 75 is molded into the handle extension returning the supply water fed through water supply schannel 73 to the turbine wheels 79 and then back to return channel 75 to the water return line 58 in the handle.

As schematically shown, appropriate pressure regulators, switches and filters may be arranged in the water supply line as desired.

It is preferred that springs 81 be arranged in the bearing recesses 80 and that sufficient clearance be provided between the bearing recesses and the wheel journals in both the FIG. 1 and the FIG. 4 embodiments to provide for a "floating" brush support.

OPERATION

In use, the aforedescribed brush assembly may be utilized in a variety of situations where it is desired to apply a brushing effect to a relatively small area such for example as a tooth surface for which the brush is particularly adapted.

The brush assembly components are fabricated utilizing conventional fabrication techniques, such for example as conventional plastic molding techniques, since the components lend themselves to ready fabrication of plastic material. The handle, and handle extension housing, are fabricated of plastics, and the desired brush supporting wheels, drive belts and/or water supply lines may similarly be fabricated utilizing conventionally available plastic forming techniques, such as molding, extrusion or the like, and the components are assembled as described.

In the FIG. 1-3 embodiments, as will be apparent to those skilled in the art, energization of the motor in the handle 15 will result in rotation of drive shaft 17 and drive gear 19, the rotation of which will be transmitted to gear 37 from which the rotation will be taken off via belt 39 and transmitted to brush drive wheels 41.

In the FIG. 4 and 5 embodiments, coupling of the water supply line to a sink faucet and opening of the top provides an energizing water supply which causes brush supporting turbine wheels to rotate with the water then passing back through return lines 75, 58 and 61 for discharge.

In the illustrated preferred embodiment, it is preferred that the brushes employed be of a hollow elastic type, with upstanding peripheral edges 55, such that upon bringing the brush surfaces against the tooth, the peripheral upstanding edges 55 will be permitted to flex both to and from the axis of rotation to thereby insure desired rubbing action in both directions of bristle movement, as compared to a conventional brush contour where the peripheral bristles are restrained from movement towards the center of the brush by the interiorally positioned bristles.

It is further found that by virtue of the contrary direction of rotation of adjacent segments of brush members 45, there is improved facility of dislodgement of undesired surface material on the surface to be cleaned, thus improving the cleaning action.

Additionally, the floating mount of the brush support serves to implement approximation of the surfaces to be cleaned by the brushes.

The above disclosure has been given by way of illustration and elucidation, and not by way of limitation, and it is desired to protect all embodiments of the herein disclosed inventive concept within the scope of the appended claims.

I claim:

1. A power driven brush assembly for cleaning teeth or the like, said assembly comprising:
   a hollow handle element;
   a hollow extension for said handle element;
   drive means providing energy to said extension;
   a plurality of brush supports in said extension at an end thereof remote from said handle element
   a power transmission between said drive means and at least two of said brush supports;
   and a plurality of brushes at least one of said brushes contoured with a cup-shaped cavity at one end thereof remote from said shaft, implementing the facility with which the outer edges of the brush may be bent to approximate the contours of the surface to be brushed said brush supports mounted in said handle extension so that adjacent brush segments move in opposed directions.

2. A power driven brush assembly as in claim 1, in which said brush supports comprise a plurality of gear wheels.

3. A power driven brush assembly as in claim 2, in which at least one of said gear wheels is belt driven.

* * * * *